(12) United States Patent
Fleischer (10) Patent No.: US 7,381,245 B2
(45) Date of Patent: Jun. 3, 2008

(54) SYSTEM FOR INFLUENCING AND TREATING THE AIR OF AT LEAST ONE ROOM

(75) Inventor: Werner Fleischer, Schwarzenberg (CH)

(73) Assignee: LK Luftqualität AG, Littau (CH)

( * ) Notice: Subject to any disclaimer, the term of this patent is extended or adjusted under 35 U.S.C. 154(b) by 0 days.

(21) Appl. No.: 10/596,384

(22) PCT Filed: Dec. 9, 2004

(86) PCT No.: PCT/EP2004/014027

§ 371 (c)(1),
(2), (4) Date: Jun. 19, 2006

(87) PCT Pub. No.: WO2005/056065

PCT Pub. Date: Jun. 23, 2005

(65) Prior Publication Data

US 2007/0165353 A1    Jul. 19, 2007

(30) Foreign Application Priority Data

Dec. 12, 2003   (DE) ................... 103 60 237
Mar. 31, 2004   (JP) ..................... 2004-104367

(51) Int. Cl.
*B03C 3/68* (2006.01)

(52) U.S. Cl. ............... 96/18; 95/2; 95/3; 95/4; 95/73; 95/78; 96/19; 96/26; 96/62; 96/64; 422/22; 422/121

(58) Field of Classification Search ........... 96/18, 96/19, 26, 60–64; 95/2–4, 73, 78; 422/22, 422/121, 186
See application file for complete search history.

(56) References Cited

U.S. PATENT DOCUMENTS

| | | | |
|---|---|---|---|
| 3,973,927 A * | 8/1976 | Furchner et al. ............ 95/3 |
| 5,035,728 A * | 7/1991 | Fang .......................... 96/19 |
| 5,259,553 A | 11/1993 | Shyu |
| 5,759,487 A * | 6/1998 | Jung .......................... 422/22 |
| 5,865,880 A * | 2/1999 | Matsui ....................... 96/26 |
| 6,040,777 A * | 3/2000 | Ammann et al. .......... 340/632 |
| 6,375,714 B1 | 4/2002 | Rump et al. |
| 6,464,754 B1 * | 10/2002 | Ford .......................... 95/26 |
| 6,602,129 B1 | 8/2003 | Sokolean et al. |
| 6,623,544 B1 * | 9/2003 | Kaura ........................ 95/3 |
| 6,723,146 B2 * | 4/2004 | Ninomiya et al. .......... 55/344 |
| 2002/0014401 A1 | 2/2002 | Fleischer |
| 2003/0086813 A1 | 5/2003 | Fleischer |

FOREIGN PATENT DOCUMENTS

| | | |
|---|---|---|
| DE | 43 34 956 A1 | 4/1995 |
| DE | 44 21 167 A1 | 12/1995 |
| DE | 10007523 A1 * | 9/2001 |
| EP | 0 756 138 A2 | 1/1997 |

* cited by examiner

*Primary Examiner*—Richard L Chiesa
(74) *Attorney, Agent, or Firm*—Gudrun E. Huckett (57) ABSTRACT

An arrangement for treating room air has a first air quality sensor in an external air conduit of an air conditioning device. An ionization apparatus, an ozone sensor, an air humidity sensor, an airflow sensor, and at least one air temperature adjusting device are arranged in the supply conduit between air conditioning device and room. Chamber or hood devices forming a component of the room are coupled to the supply conduit. A side of the chamber or hood devices has openings ensuring convection of the supply air into the room. A recirculating air conduit branches off an exhaust conduit to the air-conditioning device. A second air quality sensor is arranged in the recirculating air conduit. A control device is connected to first air quality sensor, ozone sensor, air humidity sensor, airflow sensor, second air quality sensor, and the air temperature adjusting device.

21 Claims, 6 Drawing Sheets

SYSTEM FOR INFLUENCING AND TREATING THE AIR OF AT LEAST ONE ROOM

This application is a national stage filing of International Application No. PCT/EP04/14027 filed on Dec. 9, 2004.

BACKGROUND OF THE INVENTION

The invention concerns arrangements for influencing and treating the air of at least one room by adjusting the temperature as well as by ionization of the supply air.

It is known that the air in a room and thus the breathing air can be treated by ionization apparatus. In this connection, bacteria and other germs are killed and large molecules are split into small molecule fragments. Complex and large molecules, inter alia, are smell-causing substances so that by air ionization it is also possible to suppress smells. Moreover, even health-hazardous load situations of the room air can be eliminated and microorganisms in the air can be effectively reduced.

In ionization apparatus electrical fields between two electrodes at voltage potentials are utilized in order to generate ions by gas discharge by collision ionization. As it is known in the art, for this purpose ionization tubes in the form of glass tubes are used; the inner side of the tubes is coated and the outer side is electrically conducting. For this purpose, is it is known in the art to arrange preferably tubular metal grid structures on the outer side of the glass tubes so that a coaxial configuration is provided. When an electrical voltage is applied that is sufficient for gas discharge, the glass of the wall becomes a dielectric in which a large electrical field is present. The flowing air is enriched with ions. In DE 196 51 402 A1 (Apparatus for Physical Treatment of Air, in particular, Breathing Air) air ionization devices of a flat configuration are used as electrodes that are spaced apart from one another.

A significant disadvantage of such an arrangement resides in that, starting at a certain voltage, ozone is formed and ozone formation is increased with increasing voltage.

DE 43 34 956.0 C2 (Method for Treatment of Air with Ions as well as Device for Performing the Method) discloses a method for air treatment with ions and a device for performing the method wherein the long-term stability of the ionization apparatus is increased. In this connection, the discharge voltage is controlled such that an increased ozone generation does not take place. As in the case of unloaded natural air, it is ensured technically by means of the described method and the described device that oxygen ions are present at all times. By means of the employed sensors, in the form of an air quality sensor, an air flow sensor, and an air humidity sensor, this minimum intensity can be maintained substantially within a load range.

In the presence of outer disruption sources, such as smog, an inversion weather condition, thunderstorms, outer energy fields, or inner disruption sources as a result of operating electrical devices, the ozone load in the supply air can be increased by an undesirable amount and can lead to a limit value being surpassed. In DE 100 07 523 C2 (Method for Air Treatment with Ions as well as Device for Performing the Method) an additional ozone sensor for determining the ozone contents is therefore provided as a component of this device. By means of a control device, the ionization power is controlled with regard to the ozone contents also in such a way that even ozone decomposition occurs.

EP 1 078 205 B1 (Air Cooling Element, Method for its Operation as well as Air Cooling Arrangement) discloses an air cooling element having a chamber that has at least one air inlet and is delimited at one side by a cooling wall and otherwise is essentially closed to be air tight. The cooling wall has micro holes distributed across its surface area. This solution is only provided for temperature control of a room. Moreover, several such chambers are required for a room so that gaps are visible between neighboring chambers. Accordingly, ceilings that are configured in this way are particularly not suitable for living spaces. The micro holes represent a further disadvantage because these holes must not become plugged when applying a coating to the cooling wall. In order to ensure this, complex technologies are required so that such chambers cannot be produced easily in an economic fashion.

SUMMARY OF THE INVENTION

It is an object of the invention to condition at least one room comfortably wherein a high air quality as well as a draft-free and thus comfortable air supply to the room must be ensured.

This object is solved by the following features:
- a first air quality sensor in the external air conduit of an air conditioning device,
- at least one ionization apparatus, an ozone sensor, an air humidity sensor, an airflow sensor, and at least one device for temperature adjustment of the air arranged in the supply conduit between the air conditioning device and the at least one room,
- at least one chamber-like or hood-like device forming a component of the room coupled to the supply conduit, wherein either the wall or the ceiling separating the chamber-like or hood-like device or a chamber-like or hood-like device and the room from one another has openings for ensuring convection of the temperature-adjusted and ionization-influenced supply air into the room,
- and an exhaust air conduit ending at the exterior as well as a recirculating air conduit connected to the air-conditioning device at the exhaust conduit of the at least one room,
- a second air quality sensor in the recirculating air conduit, and
- at least one control device connected to the first air quality sensor, the ozone sensor, the air humidity sensor, the airflow sensor, the second air quality sensor, and the device for temperature-adjustment of the air.

The arrangement for affecting and treating the air of at least one room by temperature adjustment as well as ionization of the supply air is characterized in particular by ensuring a high air quality and simultaneously a draft-free and thus comfortable air supply.

The high air quality is ensured by controlled ionization of the supply air of the at least one room. The control of this ionization is based on measured values of
- a first air quality sensor in the exterior air conduit of an air conditioning device,
- an ozone sensor, an air humidity sensor, and an air flow sensor in the supply conduit between air conditioning device and the at least one room, and
- a second air quality sensor in the recirculating air conduit between the at least one room and the air conditioning device.

A device for air temperature adjustment ensures proper room temperature wherein heating means as well as cooling means are provided. In this way, air conditioning of the at least one room is ensured.

The draft-free and thus comfortable air supply is based advantageously on at least one chamber-like or hood-like device that is a component of the room and is coupled to the supply conduit of the at least one room, wherein a wall that separates the chamber-like or hood-like device or the chamber-like and/or hood-like devices and the room from one another has openings for ensuring convection of the temperature-adjusted and ionization-influenced supply air into the room. These openings are designed such that the temperature-adjusted and ionization-affected air can flow into the room without creating a draft that can be sensed by persons and without creating detectable noise. In this way, the room air is influenced by radiant heat of the surface with the openings and by convection, wherein a high air flow as a laminar displacement air flow that cannot be sensed or felt by the persons in the room is provided by passing through the openings in the form of micro openings/micro pores. In this way, advantageously a compact displacement flow of ionized air is present. The mixture ratio of the room air and the supply air is achieved by injection of supply air. The air flow through these openings in the form of micro openings/micro pores leads advantageously to a temperature-adjusted and influenced air layer at the wall facing in the direction toward the room. This air flow and this air layer prevent advantageously that humid air provided with air-borne particles can reach the wall with the openings. Deposition and collection of particles as well as formation of a micro climate that would support the growth of biological particles are substantially prevented. In this way, the arrangement according to the invention can be operated over an extended period of time without requiring cleaning.

Advantageously, between the supply air and the room air a high temperature difference is present so that this process and state are advantageously supported. At the same time, a minimal air quantity is required for air conditioning. In this way, in an economically favorable way several rooms can be connected to a centrally arranged system for affecting air. Accordingly, the arrangement of the present invention is particularly suitable for buildings with several working and/or living spaces whose room height has no effect on air conditioning. The arrangement is characterized furthermore in that it can be retrofitted in already existing buildings.

A further advantage of the arrangements according to the invention resides in that the level of the ionization power of at least one or of several ionization apparatus can be controlled by the control device in such a way that, when an ozone value that is too high occurs, the ozone level is reduced by formation of free radicals as well as natural oxygen clusters as an agglomeration of electrically charged oxygen ions. In this connection, the level of ozone is measured by the ozone sensor in the supply air as a mixture of external and recirculating air. By means of the control device connected to the ozone sensor and limit values that can be set or are set therein, the ionization apparatus is controlled such that a damaging effect caused by the presence of ozone on persons within the room is prevented substantially. The control device supplies optimized alternating pulses that are supplied to the at least one ionization apparatus for providing an actually stable and nature-adequate supply air ionization wherein a predetermined ozone limit value is not surpassed and in extreme situations ozone is eliminated. Each alternating pulse is a full sine curve that is cut off when passing through zero, i.e., when the half waves change (phase control). The frequency is not changed in this connection. Advantageously, several alternating pulses in the form of several sine curves are combined to packets. The packet size and thus the number of alternating pulses per packet provides a possibility for optimizing air ionization and, at the same time, for minimizing the load on the electrical supply of the device according to the invention. The discharge voltage remains constant in this connection so that a stable air ionization is ensured. In this way, in particular a targeted utilization of the recirculating air is provided so that in particular at high temperatures in the summer and at low temperatures in the winter energy costs for cooling or heating are saved.

A further advantage of the arrangements according to the invention resides in that with the ionization of the supply air gaseous volatile hydrocarbons are decomposed, the oxidation potential of the air is lowered, and microorganisms are eliminated.

By means of a regulator for the volume flow of the supply air in the supply conduit upstream of the chamber-like or hood-like device or one of the chamber-like or hood-like devices, a comfortable climate in the room can be manually adjusted and automatically maintained. In particular, this concerns the temperature in the room. For this purpose, the regulator for the volume flow and/or the control device and/or an additional control device are connected to a temperature sensor arranged in the room. By means of an adjustable element that is connected to an additional control device and/or the control device and or the regulator, the volume flow is regulated in accordance with the selected value. The element in this connection is advantageously either a potentiometer as a continuously adjustable voltage divider or a switch in connection with resistors as a voltage divider that is adjustable in steps.

In accordance with another embodiment, several chamber-like devices are advantageously arranged in one plane wherein the chamber walls facing in the direction of the room have penetrations. In this way, constructively limited and easily mountable units are provided in which the supply air can still be distributed uniformly without great pressure differences. The penetrations can be significantly greater than the openings ensuring convection so that an economical manufacture of the chamber-like devices is provided. The openings that ensure the convection of the supply air are advantageously components of a layer that is applied to the chamber wall or a body that is arranged on the chamber walls. In this way, in particular gap-free walls can be realized. Especially by means of the second variant continuous walls can be realized wherein advantageously the layer or the body are applied or arranged after mounting of the chamber-like devices.

The cross-sections of the penetrations provided as openings of the chamber-like devices are smaller or identical or greater than the cross-sections of the openings of the body. In the case of smaller or greater openings, a laminar air flow results. In the case of identical or greater openings there is no dynamic pressure between the chamber-like devices and the body that is arranged at a spacing.

Beneficial layers are a paint coating, a stucco coating, or a coating of fiber materials that can be applied advantageously also after installation of the chamber-like or hood-like devices.

An especially advantageous realization of the wall is provided when the body is comprised of fiber materials and is a woven material, a knit material, or a non-woven material. It can be advantageously arranged loosely on the chamber wall. In this way, it is possible to remove and exchange this body independent of the chamber-like or hood-like devices. In this way, an easy cleaning of such a body is possible. Moreover, the visual appearance of the room can be easily changed.

In accordance with another embodiment, the flexible web-shaped body that spans the chamber-like and/or hood-like devices advantageously leads to the simple realization of a continuous ceiling. Interruptions or divisions are not visible. The flexible web-shaped body is easily removable or exchangeable as a whole so that it can be easily cleaned. With such an exchange, the aesthetic appearance of the room provided therewith can also be easily changed. By means of a flexible web-shaped body that is arranged at a spacing relative to the chamber-like and hood-like devices it is also possible to compensate uneven surfaces of the ceiling as well as of the chamber-like and/or hood-like devices. The chamber and/or hood-like devices advantageously enable that a substantially uniform temperature adjustment or influencing of the room air, in particular in the case of large size rooms, is possible. In this connection, the temperature-adjusted and influenced supply air flows into these devices and into the room through the openings or also micro openings of the flexible web-shaped body. Advantageously, the supply air can be swirled by means of suitable devices within the chamber-like and/or hood-like devices.

In this way, the room air is affected by radiant heat of the surface with the openings and by convection wherein through the openings, even in the form of micro openings/micro pores a high air flow is provided that is however not detectable by persons present within the room. The mixing ratio of the room air and of the supply air can be realized by the injection of supply air. The air flow through these openings in the form of micro openings/micro pores advantageously leads to the formation of a temperature-adjusted and influenced air layer on the wall facing in the direction of the room. This air flow and this air layer prevents advantageously that humid room air containing air-borne particles can reach the wall with the openings. The deposition and collection of particles as well as the formation of a microclimate that supports growth of biological particles is substantially prevented. In this way, the ceiling arrangement according to the invention can be used for a longer period of time without requiring cleaning.

Moreover, the ceiling arrangement is characterized advantageously also in that it can be easily retrofitted in already existing buildings.

The flexible web-shaped body is comprised advantageously of fiber materials or a layer of fiber materials. In this connection, the flexible web-shaped body is a fabric, a woven material, a knit material, or a non-woven material having the micro openings. Such bodies are also known textiles.

Such bodies can be in particular also designed to have different colors so that at the same time this body is a decorative element of the room.

Advantageously, the flexible web-shaped body is the upper cover of the room as well as an intermediate ceiling of the room.

In order to ensure fire protection in buildings, the layer, the body or the flexible web-shaped body or at least the layer arranged facing in the direction of the room of the layer system that represents the flexible web-shaped body is comprised of a material that is not easily flammable or is a nonflammable material or a corresponding layer is applied onto said body or said layer.

Profiled bodies with several openings or grooves for spreading elements form a frame and this advantageously leads to the flexible web-shaped body being detachably tensioned. By positioning the frame with the flexible web-shaped body underneath the chamber-like and/or hood-like devices, the flexible web-shaped body can be arranged substantially without any unevenness. The profiled bodies have first openings or grooves for spreading means as second spreading means connected to the ceiling that are also formed as frames having matching dimensions. In the case of openings in one wall of the profiled body they are provided with several cavities while in the case of grooves the profile bodies represent a body. In the first variant, the spreading parts of the spreading means are arranged in the respective cavity while in the second variant the spreading parts are arranged in the grooves. The lengths of the profiled bodies and thus also of the first openings or grooves and the spreading means are advantageously identical so that a safe and fixed securing action of the frame with flexible web-shaped bodies is provided. A wall or surface of the profiled bodies that is arranged angularly to the surface of the profiled bodies provided with the first openings or grooves has also at least one opening or groove, respectively, for the end area of the flexible web-shaped body and spreading means as a first spreading means. The lengths of the profiled bodies and of the first spreading means are identical so that a safe securing action of the fabric or flexible web-shaped body is realized. The second openings or grooves face outwardly in the case of profiled bodies arranged as a frame, respectively, so that the flexible web-shaped body spans the frame itself. In this way, a surface completely formed by the flexible web-shaped body is provided.

The thus provided fastening and tensioning device for the flexible web-shaped body is characterized furthermore by an easy mounting possibility. The frame formed by the profiled body is provided with the flexible web-shaped body. When doing so, the fabric and the flexible web-shaped body are tensioned. By means of the first spreading means, this can be easily realized. Subsequently, mounting of the frame with the tensioned flexible web-shaped body on the ceiling is realized wherein the frame is simply pressed against it such that the spreadable components of the second spreading means are placed into the first openings or grooves.

The first spreading means and the second spreading means are parts of spreading connections that represent positive-looking connections. In the case of detachable spreading connections, elastic deformations in corresponding grooves or recesses lead to fixed detachable connections. The cavities/openings or grooves of the profiled bodies and the spreading means form so-called snap-in connections. In the case of the second openings or grooves in the profiled bodies and the first spreading means by means of these snap-in connections advantageously at the same time the attachment of the end areas of the fabric or of the flexible web-shaped body is realized and thus of the fabric or the flexible web-shaped body itself.

Advantageously, the profiled body has at least two cavities separated from one another by a partition so that a profiled body having the first opening and the second opening is realized. The length of the openings and the length of the profiled body are identical so that spreading means of the same length can be placed. In this way, a fixed securing action of the fabric or the flexible web-shaped body on the frame as well as of the frame together with the fabric or the flexible web-shaped fabric on the wall or the ceiling is realized.

In a preferred embodiment the flexible web-shaped body does not completely rest against the frame. In this way, a covering of the flexible web-shaped body is possible substantially without any unevenness.

Expedient configurations of the spreading means are either two arc-shaped legs or to legs positioned angularly relative to one another that are spaced apart from one another, respectively.

In one embodiment the profiled body has at least three cavities that are separated by two partitions from one another, and this leads advantageously to end areas of corner elements being insertable into a cavity that is closed off in the circumferential direction. In this way, a frame is easily realized with the profiled bodies and the corner elements.

A favorable tensioning and fastening device is provided in that the end area of the body is located in the clamping mechanism or between the clamping mechanism as well as a wall of a frame arrangement or between the clamping mechanism as well as a wall of the room. The end area of the body has a thicker portion, and the body is a plastic film that expands upon heating. The end areas of the film in the aforementioned and therefore expanded state are inserted into the clamping mechanism or between the clamping mechanism and a wall of the frame arrangement. Upon cooling of the film, the dimensions of the film will be reduced so that the film itself will cause its tensioning. For improved securing action and placing of the film, the film has in its end area a thicker portion.

A favorable realization for determining the height of the ionization power of the ionization apparatus, wherein the ionization is realized by electrical discharge on ionization tubes or corona discharge tubes, is realized by measuring in particular the volatile hydrocarbon load of the external air by means of the first air quality sensor, the flow velocity or the volume flow of the air to be treated by means of the air flow sensor, the relative humidity of the air to be treated by the air humidity sensor, the contents of ozone in the supply air by means of the ozone sensor, and the oxidizable air components of the exhaust air and/or recirculating air by means of the second air quality sensor.

The ionization apparatus is operated such that a minimum intensity of oxygen ions in accordance with natural conditions is ensured. For this purpose, the ionization apparatus is operated constantly so that the air supplied to the room is influenced at all times. For suddenly changing conditions, for example, caused by several smokers in the room or by strongly acting cleaning agents or increasing loads of the external air, the time constant is significantly shortened for an effective ionization so that the room air is influenced more quickly in a positive way or is immediately neutralized.

The ionization power of the at least one ionization apparatus is controlled such that it is increased for increased proportion of volatile hydrocarbons and/or increase of air velocity and/or increase of relative humidity of the air and/or increased proportion of oxidizable air components. In this way it is ensured that, in the case of diminishing properties of the air quality in the room, substantially unloaded supply air is supplied to the room or to the waiting area by means of the predetermined air change and the optimized intensity.

A favorable control of the ionization apparatus is provided by a temporally supplied periodic alternating voltage. In this connection, the ionization apparatus is supplied with an alternating pulse, alternating pulses, or alternating pulses combined to packets of an available periodic alternating voltage. Advantageously, the optimized discharge voltage is constant in this connection.

The proportion of ozone is lowered such that the desired and preset limit values of a comfortable climate in the room are ensured. In a first range, the power of the ionization apparatus is lowered for this purpose. When the value of the ozone contents of the supply air increases despite lowering of air ionization, at least one external ozone source is present. In this case, automatically a mode for decomposition of ozone is switched on by the control device. When the preset limit values are reached again, the ionization apparatus is returned to normal operation. The energy level of the ozone is changed such that it decomposes. The values for signalization are selected such that sufficient reaction safety is provided.

BRIEF DESCRIPTION OF THE DRAWINGS

One embodiment of the invention is illustrated in the drawings and will be explained in the following in more detail.

It is shown in.

DESCRIPTION OF PREFERRED EMBODIMENTS

Figure 1:
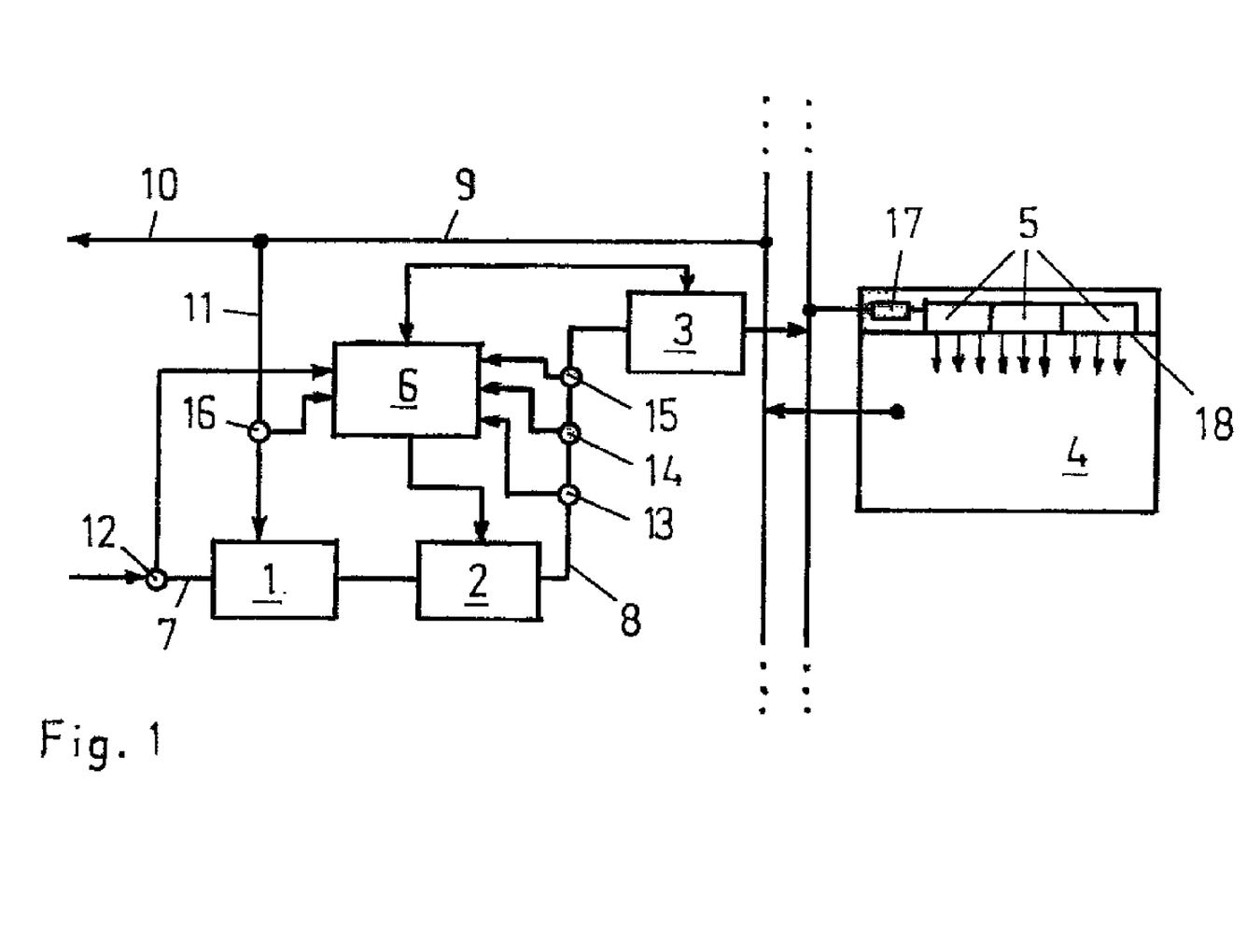
FIG. 1 a principal schematic illustration of an arrangement for influencing and treating the air of at least one room.

An arrangement for influencing and treating the air of at least one room 4 is essentially a combination of devices for temperature adjustment as well as for ionization of the supply air of at least one room 4.

In the external air conduit 7 of an air-conditioning device 1 a first air quality sensor 12 is arranged. In the supply conduit 8 between the air-conditioning device 1 and the at least one room 4, at least one ionization apparatus 2, an ozone sensor 13, an air humidity sensor 14, an airflow sensor 15, and at least one device 3 for temperature adjustment of the air are connected. Several chamber-like devices 5 that are components of the room 4 are coupled to the supply conduit 8. To the exhaust conduit 9 of the at least one room 4 an exhaust air conduit 10 that ends outside as well as a recirculating air conduit 11 connected to the air-conditioning device 1 are provided. In the recirculating conduit 11 a second air quality sensor 16 is arranged. The first air quality sensor 12, the ozone sensor 13, the air humidity sensor 14, the airflow sensor 15, and the second air quality sensor 16 are connected to at least one control device 6. The control device 6 is connected to the ionization apparatus 2 and the device 3 for temperature adjustment of the air. In the supply conduit 8 upstream of one or a first chamber-like device 5 a regulator 17 for the volume flow of the supply air is connected. The drive of the adjusting element of the regulator 17 is also connected to the control device 6 and/or an additional control device for the room temperature.

FIG. 1 shows such an arrangement for influencing and treating the air of at least one room 4 in a principal schematic illustration.

The device 3 for temperature adjustment of the air is a known heating device and/or cooling device for air.

Several chamber-like devices 5 are arranged in one plane on the ceiling of the room 4. The cavities of the chamber-like devices 5 are connected by pipelines to one another such that via the supply conduit 8 downstream of the device 3 for air temperature adjustment the supply air can flow into the chamber-like devices 5. The chamber walls of the devices 5 facing in the direction toward the room have several openings that are referred to in the following as penetrations. On or spaced from these chamber walls, a body 18 is arranged that has openings for ensuring convection of the temperature-adjusted and ionization-influenced supply air into the room 4. These chamber walls and the loosely arranged body 18 form a wall of the room 4 and thus form an intermediate ceiling of the room 4. The openings as micro openings or micro pores, in particular in an embodiment as textile materials/fiber materials are in regard to their dimensions significantly smaller than the penetrations in the chamber walls of the chamber-like devices 5. In another embodiment, the cross-sections of the penetrations can be designed to have the same size or to be greater than the cross-sections of the openings. The body 18 is comprised either of fiber materials and is a woven material, an interlaced material, a knit material, or a non-woven material or is a plastic film or is comprised of a composite material as a combination of the aforementioned materials. The chamber-like devices 5 are attached to the ceiling of the room 4. The body 18 is detachably tensioned such that the chamber walls with the penetrations of the chamber-like devices 5 rest loosely directly against the body 18 or are arranged correspondingly at a spacing relative to the body 18. The body 18 is comprised moreover of a material that is not easily flammable or nonflammable.

The level of the ionization power of the ionization apparatus 2, wherein the ionization is realized by electrical discharge on ionization tubes or on corona discharge tubes, is automatically adjusted by the control device 6 as a function of the measured values of in particular the load of the external air with volatile hydrocarbons measured by the first air quality sensor 12;

the contents of ozone in the supply air by means of the ozone sensor 13;

the relative humidity of the air to be treated by means of the air humidity sensor 14;

the flow velocity or volume flow of the air to be treated by means of the airflow sensor 15; and the oxidizable air components of the exhaust air and/or recirculated air with the second air quality sensor 16.

For this purpose, in the control device 6 the signals derived from the measurements carried out by the first quality sensor 12, the ozone sensor 13, the air humidity sensor 14, the airflow sensor 15, and the second air quality sensor 16 are combined with one another such that the control device 6 sends a situation-appropriate output in the form of alternating pulse rates or several alternating pulse rates combined to packets to the ionization apparatus 2 when a higher air quantity and/or a greater relative air humidity and/or greater room air load with volatile hydrocarbons—vaporous organic compounds (VOC)—or a greater oxidizing potential of the external air occurs. In this connection, an increase of the alternating pulse rates or of the alternating pulse rates combined in packets is realized. For this purpose, in the control device the following happens:

weighting the individual parameters and combining them as a sum of the individual parameters, combining as a product the individual absolute values of the parameters, or carrying out a different mathematical treatment, so that the ionization apparatus is operated at optimal efficiency.

Figure 2:
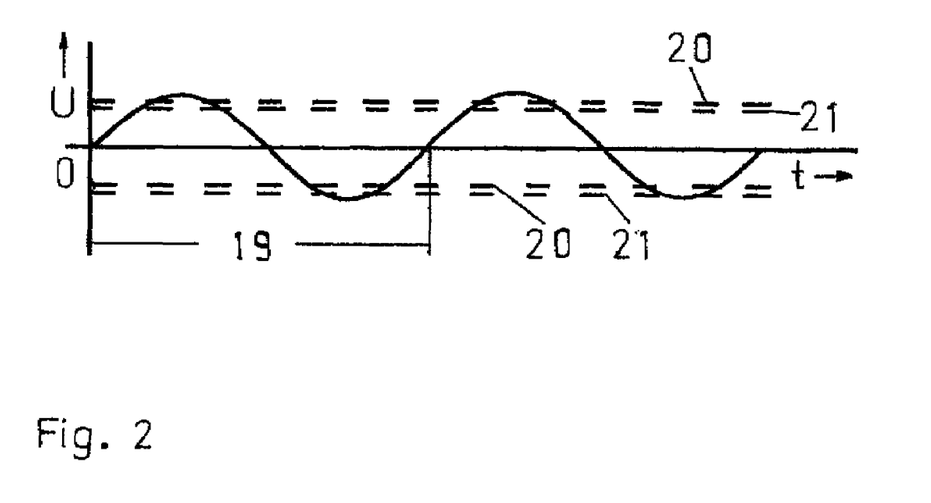
FIG. 2 a principal illustration of an alternating pulse for controlling an ionization apparatus of the arrangement.

The ionization apparatus 2 is operated with temporal sequences of periodic alternating voltage of identical or almost identical amplitude. The smallest unit of the sequence is a period of the periodic alternating voltage as an alternating pulse 19 (illustration in FIG. 2).

Periods of the periodic alternating voltage that are not required are discharged. In this way it is ensured that the voltage during discharge remains constant. In this connection, the periodic alternating voltage has a frequency that corresponds to the frequency made available, respectively, by the power grid of the power supply so that a frequency converter is not required. The stable air ionization and thus an optimal efficiency, i.e., a high proportion of positively and negatively charged oxygen ions having a high bonding tendency—for example, with the VOC proportion of the air—and with a minimal proportion of radicals in the air is generated only by means of a defined discharge voltage. The discharge voltage must be maintained substantially constant so that the tolerance range is maintained. In connection with the illustration in FIG. 2, subsequently the behavior of the discharge during change of the discharge voltage upon surpassing the limit 20 and dropping below the limit 21 of the tolerance range between limits 20, 21 of an optimal discharge voltage will described. When the limit 20 is surpassed by increasing the voltage of the ionization apparatus 2, progressively the ozone load in the supply air will increase. When the discharge voltage on the other hand drops below the limit 21, a working field of air ionization results which is characterized by a spontaneous discharge (buffering effect) wherein also undesirable oxygen radicals or ozone is released. Accordingly, a defined discharge voltage is kept constant in the process. A situation-appropriate and stable air ionization is obtained by an appropriate activation of the sine curve of the defined alternating voltage that is cut off when passing through zero. In this connection, such a sine curve is an alternating pulse 19, respectively, that activates the ionization apparatus 2. For further optimization of the efficiency of the air ionization, the control device 6 is designed such that additionally the alternating pulse rates can be combined to meaningful packets or sets of a certain number of alternating pulses.

The signals of the ozone sensor 13 are evaluated as follows or used in the process:

no influencing action when the ozone proportion in the supply flow is from 0 to 0.06 ppm;

lowering the momentary ionization power to 50 percent when ozone proportion greater/identical to 0.06 ppm;

upon further increase of the ozone proportion, an external ozone source is present and the described measures for decomposition of ozone are initiated.

The operation is continued such that ionization takes place at all times even when extremely low process data are present wherein the first air quality sensor 12, the ozone sensor 13, the air humidity sensor 14, the airflow sensor 15, and the second air quality sensor 16 signalize that actually no ionization would have to be carried out. In this connection, an adequate natural effect is fulfilled.

During operation of the device by means of the exhaust air conduit 10 only a small amount of exhaust air is removed which is counterbalanced by a corresponding quantity of external air that is supplied through the external air conduit 7. In this way, a targeted utilization of the recirculating air for the purpose of energy conservation is achievable.

For optimizing the required energy, advantageously a constantly adjusted ratio of external air and recirculating air is possible. This ratio depends inter alia on the external air temperature, the $CO_2$ contents of the room air, a change of the room temperature, and a change of the room enthalpy.

The adjusting element of the regulator 17 for the volume flow of the supply air in the supply air conduit 8 upstream of the or one of the first chamber-like devices 5 can be connected to the control device 6 and/or an additional control device for the room temperature. In the latter case, an arrangement for affecting and treating the supply air advantageously can be combined with an already installed and thus already present arrangement for temperature adjustment of the room air to form an to an arrangement according to the invention.

Figure 3:
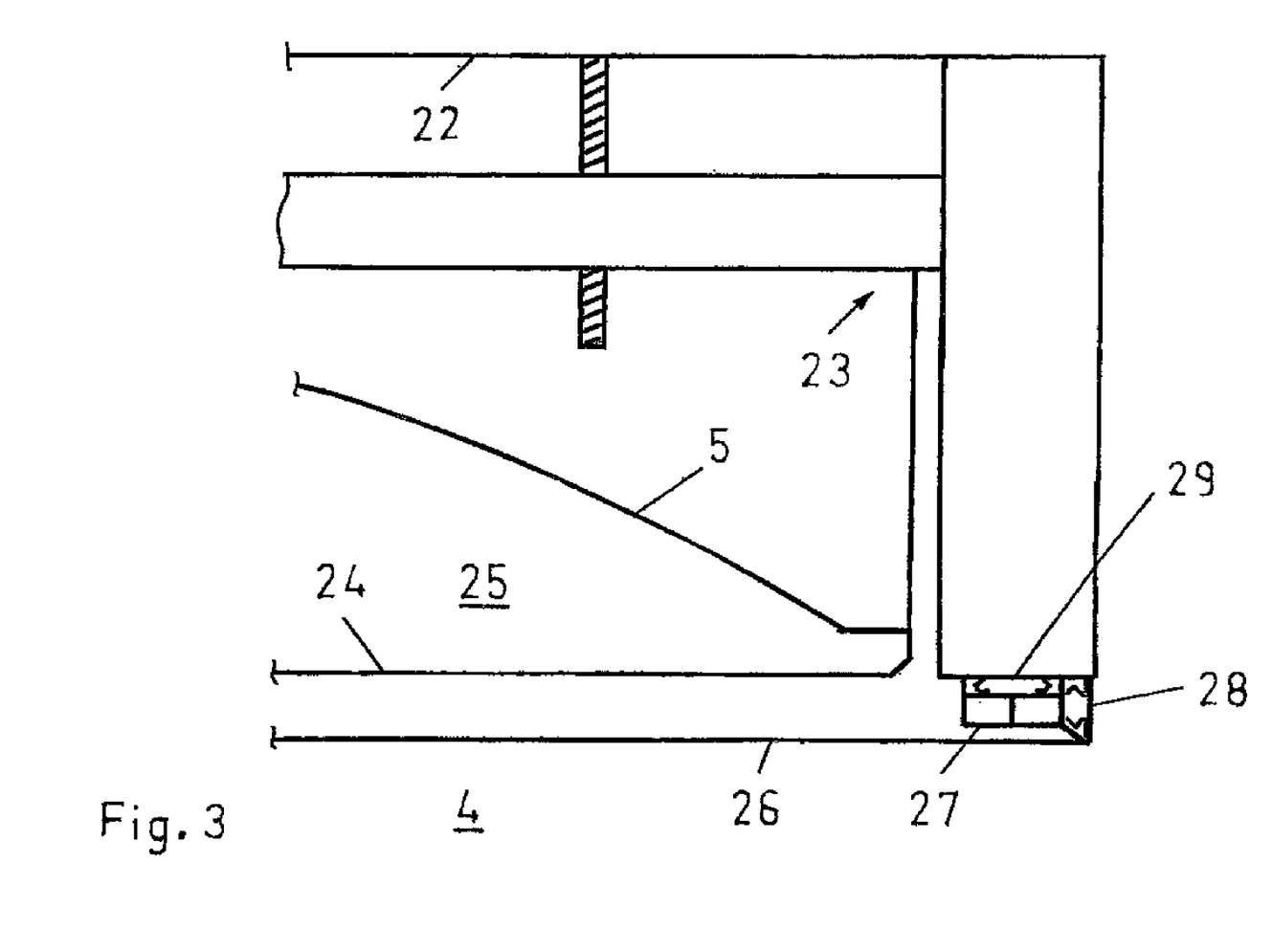
FIG. 3 a ceiling arrangement for a temperature-adjustable room and/or for affecting the properties of the room air in a principal partial view of a corner of the room.

A ceiling arrangement for an arrangement according to the invention for influencing and treating the air at least of one room 4 by temperature adjustment as well as ionization of the supply air is comprised according to one embodiment essentially of several chamber-like devices 5 arranged in one plane; a flexible web-shaped body 26 with openings even as micro openings; and a tensioning and fastening device for detachably tensioning the flexible web-shaped body 26.

FIG. 3 shows in a principal partial view a ceiling arrangement for a room 4 to be temperature-adjusted and/or for influencing the properties of the air of a room 4.

The chamber-like devices 5 are attached with devices 23 on the ceiling 22 of the room 4 such that the ceiling surface is substantially completely covered. Such devices 23 are known and FIG. 3 shows only a principal illustration. The chamber walls 24 facing in the direction of the room 4 of the chamber-like devices 5 have penetrations distributed across the surface. Moreover, these surfaces have fixed dimensions so that the rooms 4 with different surfaces can be provided easily with such chamber-like devices 5. Advantageous dimensions are up to 60 by 60 $cm^2$, respectively. The cavities 25 of the chamber-like devices 5 are connected to one another by pipelines, wherein one pipeline ends at the exterior as a connection for all chamber-like devices 5. In this way, a device for influencing and treating supply air and/or a device for temperature adjustment of supply air can be connected. The chamber-like devices 5 are comprised preferably of a sheet metal or plastic material.

Underneath these chamber-like devices 5 the flexible web-shaped body 26 is provided in a clamping and fastening device and spans the chamber walls 24 with the penetrations. The micro openings enable convection of temperature-adjusted and/or influenced supply air.

The cross-sections of the penetrations as openings of the chamber-like devices 5 are smaller or identical or greater than the cross-sections of the openings of the flexible web-shaped body 26. In particular in the case of openings that are greater in comparison to the penetrations, advantageously no dynamic pressure and no unevenness caused by it are generated by the flowing ionized air between the chamber-like devices 5 and the flexible web-shaped body 26.

Figure 4:
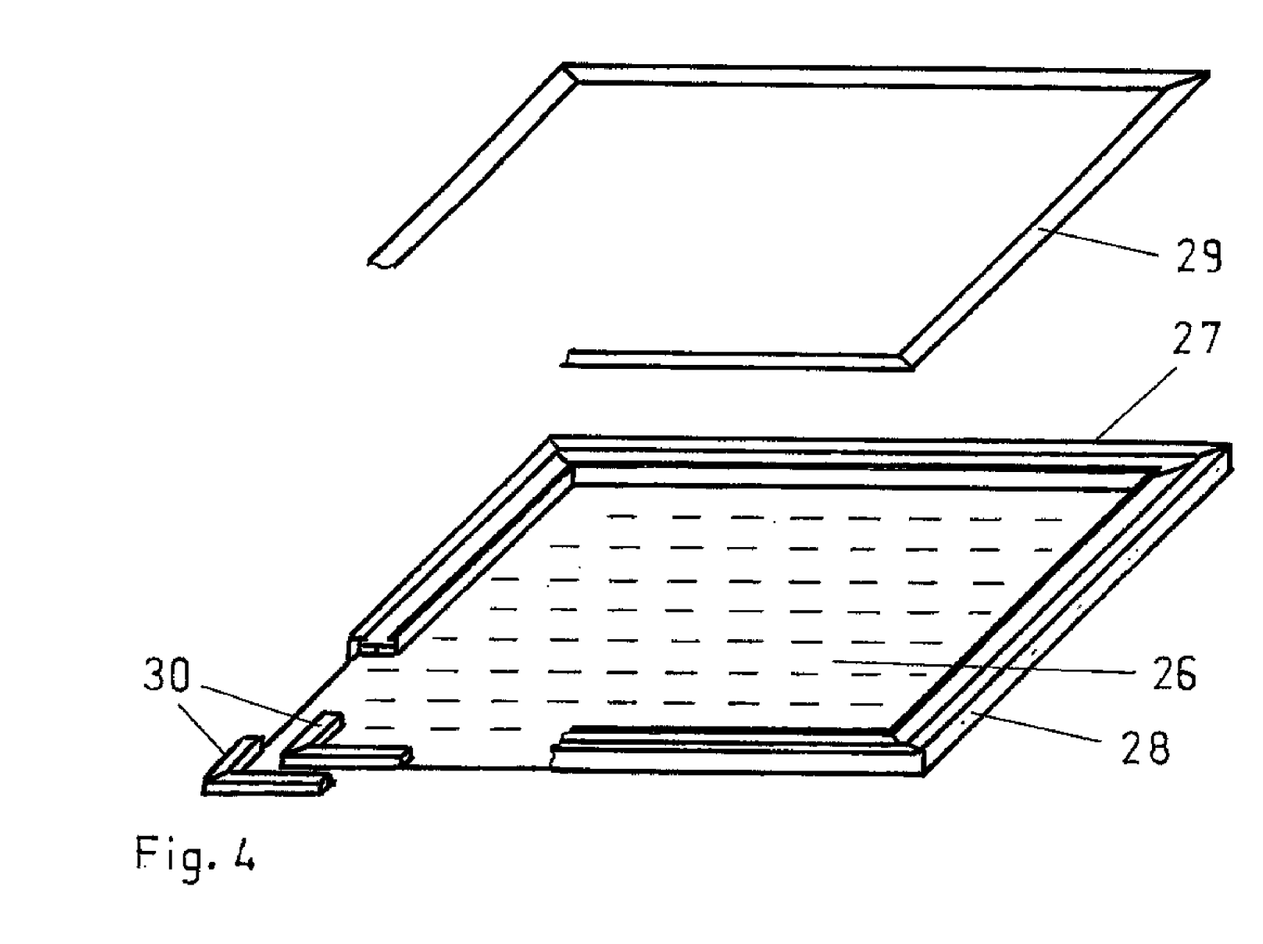
FIG. 4 a tensioning and fastening device for detachably tensioning a flexible web-shaped body.

For the tensioning and fastening device several profiled bodies 27 are arranged to form a frame (illustration in FIG. 4). The profiled body 27 itself has four cavities 33, 34, 35, 36 separated by three partitions (illustration in FIG. 5). Two body walls of the profiled member 27 positioned at a right angle to one another have in a longitudinal direction a first continuous opening 31 and a second continuous opening 32, respectively. In this way, the first cavity 33 is accessible from the exterior through the first opening 31 and the second cavity 34 through the second opening 32. The widths of the first opening 31 and of the second opening 32 are smaller than the respective dimensions of the first cavities 33 and the second cavity 34 in this direction (illustration in FIG. 5). The third cavity 35 and the fourth cavity 36 have a closed circumference. The end areas of the corner elements 30 are placed into the end areas of the profiled bodies 27 such that in a simple way a frame can be realized (illustration in FIG. 4). The frame with the profiled bodies 27 is designed such that the first openings in the direction of the ceiling 22 of the room 4 and the second openings 32 face outwardly.

Figure 5:
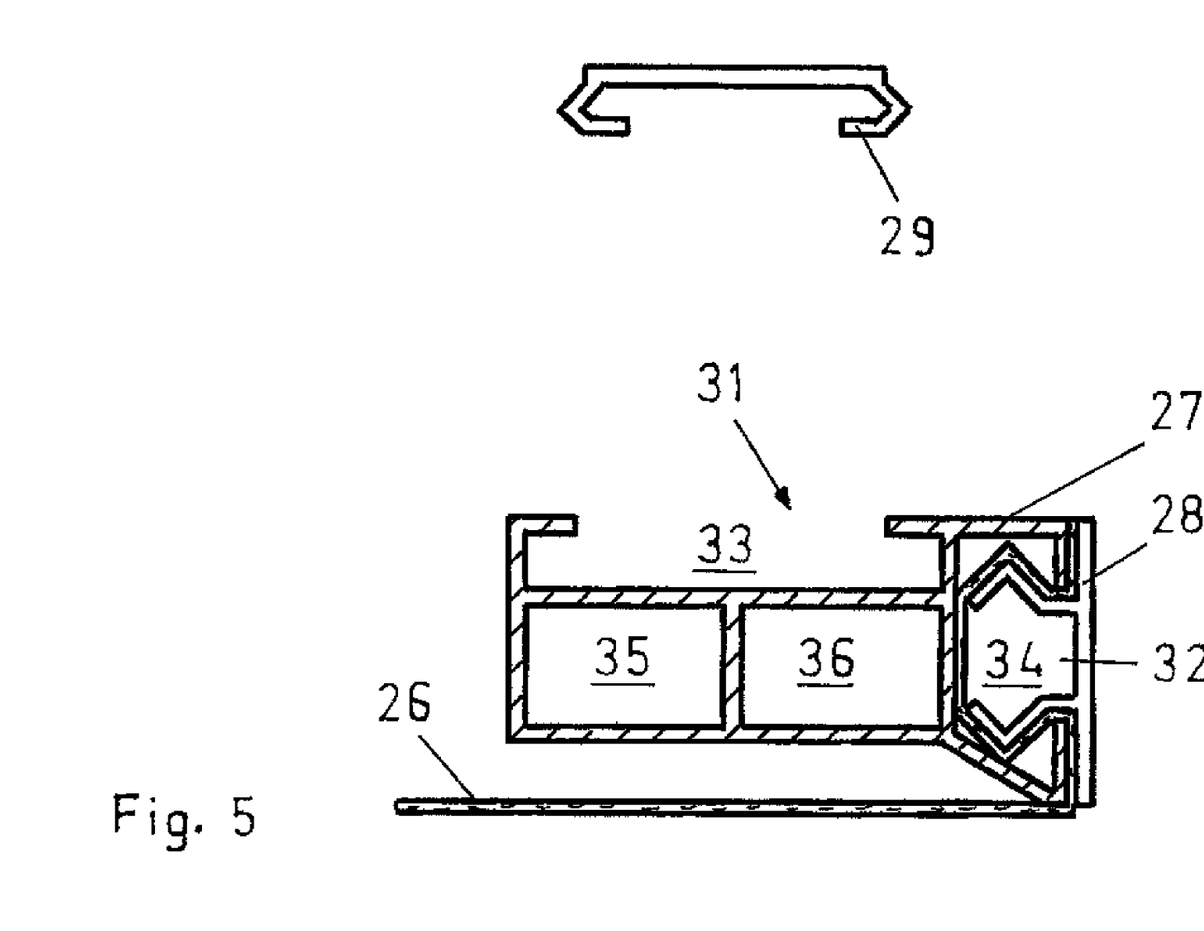
FIG. 5 components of a tensioning and fastening device for detachably tensioning a flexible web-shaped body in its profiled section.

In the second openings 32 a first spreading means as a tensioning profiled body 28 is provided. It is comprised of a plate-shaped body with two spaced-apart legs. Each of the legs has two angled partial legs and the corners face away from one another. The spacing of the legs is smaller than the width of the second opening 32 and the spacing of the angled partial legs is greater than the width of the second opening 32. The legs are positioned substantially within the second cavity 34 in the mounted state of the tensioning profiled body 28. In the tensioned state, the end areas of the flexible web-shaped body 26 are located on the tensioning profiled bodies 28 and partially between surfaces of the profiled bodies 27 and the tensioning profiled bodies 28. The lengths of the tensioning profiled body 28 and of the profiled body 27 are preferably identical. FIG. 5 shows in a section view inter alia a profiled body 27, a flexible web-shaped body 26 in a tensioned state, and a tensioning profiled body 28.

In the tensioned state, the flexible web-shaped body 26 spans the surfaces of the profiled body 27 positioned opposite the surface with the first openings 31. In this way, a frameless surface of the flexible web-shaped body 26 for mounting on elements on the ceiling 22 of the room 4 is provided.

The outer areas of the surfaces of the profiled body 27 spanned by the flexible web-shaped body 26 are slantedly arranged wherein a body wall of the profiled body and having the second opening 32 and the slantedly arranged wall area are positioned at an angle of less than 90 degrees relative to one another. In this way, it is ensured that the areas of the flexible web-shaped body 26 spanning the profiled body 27 mostly do not rest against the profiled bodies 27.

In the first openings 31 and the first cavities 33 of the profiled body 27 second spreading elements as fastening profiled bodies 29 are provided. These fastening profiled members 29 are fastened in the form of a frame to the elements connected to the ceiling 22 of the room 4 wherein the dimensions are correspondingly identical. In FIGS. 4 and 5, the frame with the flexible web-shaped body 26 and the fastening profiled bodies 29 are illustrated separately. A fastening profiled member 29 is comprised of a plate-shaped body with two spaced apart legs. Each of the legs has two angled partial legs and a third partial leg that is arranged parallel to the plate-shaped body wherein the corners of the first and of the second partial legs face away from one another. The spacing of the legs is smaller/identical to the width of the first opening 31 and the spacing of the angled partial legs is greater than the width of the first opening 31. In the mounted state of the fastening profiled body 29, the legs are positioned within the first cavity 33 so that the plate-shaped body of the fastening profiled body 29 and the body wall of the profiled body 27 form a plane. The third partial legs serve for increasing stability of the fastening profiled body 29.

The attachment of the fastening profiled body 29 is advantageously realized by screws. The spreading means of the tensioning profiled body 28 and fastening profiled body 29 are comprised preferably of plastic material and the profiled body 27 of light metal, particularly aluminum.

Figure 6:
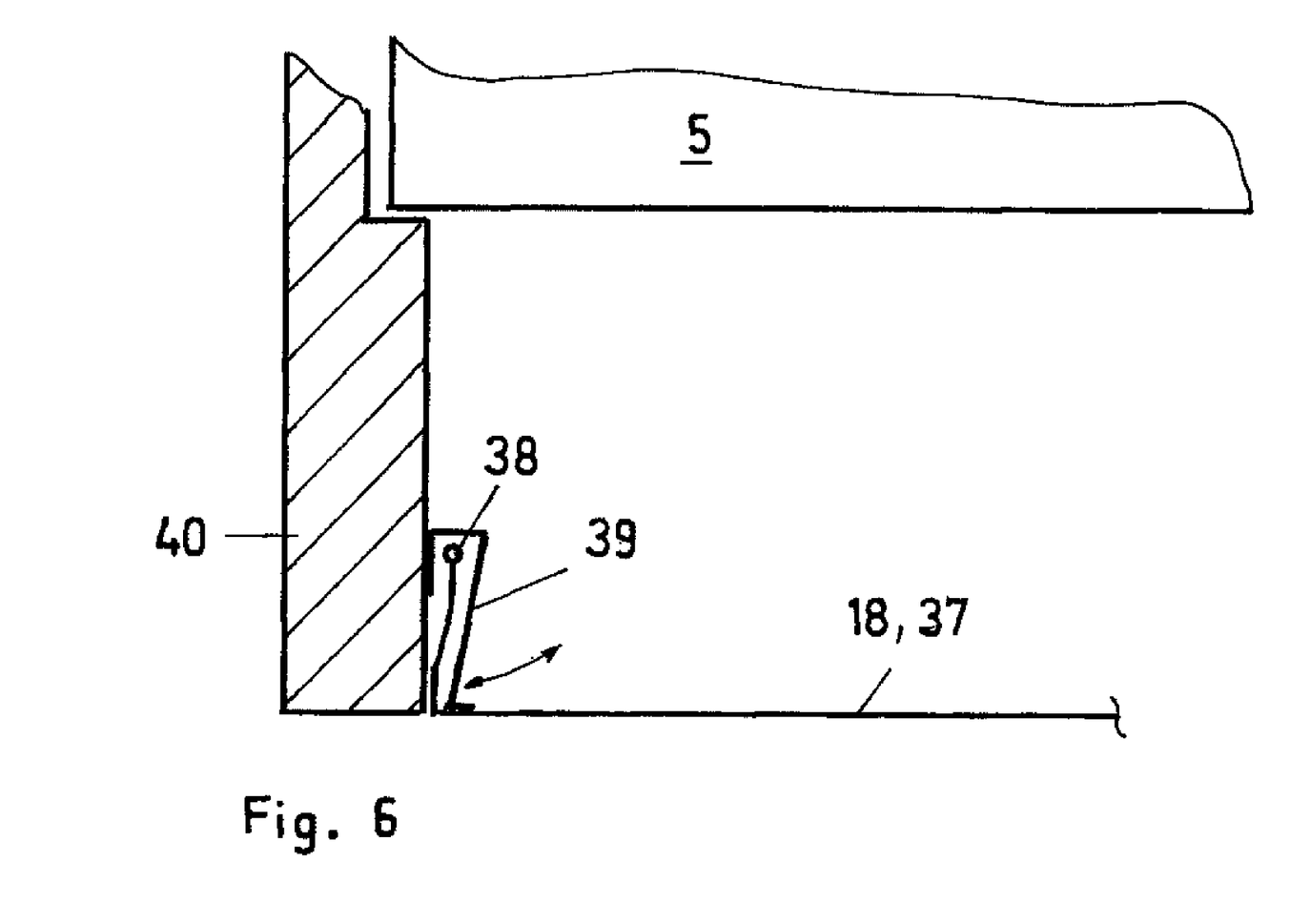
FIG. 6 a further tensioning and fastening device for detachable tensioning a flexible web-shaped body.

A further tensioning and fastening device in accordance with a further embodiment is a springy clamping mechanism 39 (illustration in FIG. 6). In this connection, the end area of the body 18 in the form of a plastic film 37 that expands upon heating is arranged:

in the clamping mechanism 39, or
between the clamping mechanism 39 and a wall of a frame arrangement 40, or
between the clamping mechanism 39 and a wall of the room 4.

The clamping mechanism 39 is advantageously a spring arrangement. For an easy and simple arrangement of the end areas of the film 37, the film is provided in its end area with a thicker portion 38.

The frame arrangement 40 for the film 37 at the ceiling of the room 4 can also receive the exhaust air conduit 9 as a channel wherein walls of the inlet openings are provided with inlet openings for the exhaust air of the room 4.

What is claimed is:

1. Arrangement for influencing and treating the air of at least one room by temperature adjustment as well as ionization of the supply air, the arrangement comprising:
    a first air quality sensor (12) in the external air conduit (7) of an air conditioning device (1),
    at least one ionization apparatus (2), an ozone sensor (13), an air humidity sensor (14), an airflow sensor (15), and at least one device (3) for temperature adjustment of the air arranged in the supply conduit (8) between the air conditioning device (1) and the at least one room (4),
    at least one chamber-shaped or hood-shaped device (5) forming a component of the room (4) coupled to the supply conduit (8), wherein either the wall or the ceiling separating the chamber-shaped or hood-shaped device (5) or the chamber-shaped or hood-shaped device (5) and the room (4) from one another has openings for ensuring convection of the temperature-adjusted and ionization-influenced supply air into the room (4),
    and an exhaust air conduit (10) ending at the exterior as well as a recirculating air conduit (11) connected to the air-conditioning device (1) at the exhaust conduit (9) of the at least one room (4),
    a second air quality sensor (16) in the recirculating air conduit (11), and
    at least one control device (6) connected to the first air quality sensor (12), the ozone sensor (13), the air humidity sensor (14), the airflow sensor (15), the second air quality sensor (16), and the device (3) for temperature-adjustment of the air.

2. Arrangement according to claim 1, wherein in the supply air conduit (8) upstream of the chamber-shaped or hood-shaped device (5) or one of the chamber-shaped or hood-shaped devices (5) a regulator (17) for the volume flow of the supply air is connected and wherein the drive for a control element of the regulator (17) for the volume flow of the supply air is connected to a control device and/or a control device in the room (4) and/or to the control device (6).

3. Arrangement according to claim 1, wherein several chamber-shaped devices (5) are arranged in one plane, wherein chamber walls facing in the direction toward the room (4) have openings as penetrations, wherein at least one layer on these chamber walls or a body (18) arranged loosely on these chamber walls or a body (18) positioned at a spacing from these chamber walls has the openings that ensure the convection of the temperature-adjusted and ionization-influenced supply air into the room (4), wherein these chamber walls with the layers or these chamber walls and the loosely arranged body (18) are the wall or the ceiling as an intermediate ceiling.

4. Arrangement according to claim 3, wherein the cross-sections of the penetrations as openings of the chamber-shaped devices (5) are smaller or identical or greater than the cross-sections of the openings of the body (18).

5. Arrangement according to claim 3, wherein the layer is a paint layer, a stucco layer, or a layer of fiber materials.

6. Arrangement according to claim 3, wherein the body (18) is comprised of fiber materials and wherein the body (18) is a fabric, a woven material, a knit material, or a non-woven material.

7. Arrangement according to claim 1, wherein several chamber-shaped and/or hood-shaped devices (5) are arranged in one plane, wherein the chamberwall (24) of the chamber-shaped device (5) facing in the direction of the room (4) has penetrations and wherein the cavity of the hood-shaped device is open in the direction toward the room (4) in that the cavities (25) of the chamber-shaped and hood-shaped devices (5) are connected to one another, and wherein a flexible web-shaped body (26) provided with openings or micro openings and enabling in this way the convection of temperature-adjusted and/or influenced supply air spans by means of a tensioning and fastening device the chamber walls (24) of the chamber-shaped devices (5) facing in the direction of the room (4) and/or cavities of the hood-shaped devices.

8. Arrangement according to claim 7, wherein the flexible web-shaped body (26) is either a plastic film or comprised of fiber materials and wherein the flexible web-shaped body (26) is a fabric, a woven material, a knit material or a non-woven material or wherein the flexible web-shaped body (26) is a layer system wherein at least one layer is comprised of fiber materials.

9. Arrangement according to claim 7, wherein the flexible web-shaped body (26) is the upper cover of the room (4) as well as an intermediate ceiling of the room (4).

10. Arrangement according to claim 7, wherein the layer, the body (18) or the flexible web-shaped body (26) is comprised of a material that is not easily flammable or a non-flammable material or wherein the layer, the body (18) or the flexible web-shaped body (26) is provided with at least one layer that is not easily flammable or a non-flammable layer.

11. Arrangement according to claim 7, wherein profiled bodies (27) forms a frame as a component of the tensioning and fastening device with the flexible web-shaped body (26), wherein two angularly positioned body walls of a profiled body (27) in a longitudinal direction have at least one first continuous opening (31) or groove, respectively, and at least one second continuous opening (32) or groove, wherein the first openings (31) or grooves of the profiled bodies (27) face in the direction of the chamber-shaped and/or hood-shaped devices (5) and the second openings (32) or grooves face outwardly, in the second openings (32) or grooves a first spreading means is arranged, wherein the flexible web-shaped body (26) spans the surfaces of the profiled bodies (27) opposite the surfaces with the first openings (31) or grooves and is arranged in the second openings (32) or grooves and is resting against the first spreading means, in the first openings (31) or grooves second spreading means are located, and on the ceiling (22) of the room (4) or on elements attached thereto the second spreading elements are fastened.

12. Arrangement according to claim 11, wherein the profiled body (27) has at least two cavities separated from one another by a partition.

13. Arrangement according to claim 11, wherein the profiled body (27) is embodied such that the body wall or body wall area of the profiled body (27) spanned by the flexible web-shaped body (26) is not parallel to the surface with the first openings (31) or grooves, wherein the outer area of the frame has the greatest spacing.

14. Arrangement according to claim 11, wherein the spreading means has two spaced-apart arc-shade legs wherein the arcs face away from one another or wherein the spreading means has two spaced-apart legs and wherein at least two partial legs are arranged at an angle to one another such that the corners face away from one another.

15. Arrangement according to claim 11, wherein the profiled body (27) has at least three cavities separated from one another by two partitions, wherein two of the cavities are accessible through openings and also components of the spreading means are arranged therein and wherein the third cavity is limited by body wall areas as well as partition areas of the profiled body (27), and wherein in the third cavity an end area of a corner element (30) is located.

16. Arrangement according to claim 7, wherein the tensioning and fastening device is a springy clamping mechanism (39), wherein the end area of the body (18) is arranged in the clamping mechanism (39) or between the clamping mechanism (39) and a wall of a frame arrangement (40) or between the clamping mechanism (39) and a wall of the room (4), wherein the end area of the body (18) has a thicker portion (38), and wherein the body (18) is a plastic film (37) that expands upon heating.

17. Arrangement according to claim 1, wherein the level of the ionization power of the ionization apparatus (2) is determined, the ionization being realized by electric discharge on ionization tubes or corona discharged tubes, in accordance with measurements of:
   in particular load of the external air with volatile hydrocarbon by means of the first air quality sensor (12),
   contents of ozone in the supply air by means of the ozone sensor (13),
   relative humidity of the air to be treated by the air humidity sensor (14),
   the flow velocity or volume flow of the air to be treated by means of the airflow sensor (15), and
   the oxidizable air components of the exhaust air and/or recirculating air by means of the second air quality sensor (16).

18. Arrangement according to claim 17, wherein the control device (6) and the ionization apparatus (2) are connected such that at all times oxygen ions are present in the supply conduit (8).

19. Arrangement according to claim 17, wherein the control device (6) and the ionization apparatus (2) are connected such that the ionization power increases when an increase of the proportion of volatile hydrocarbons and/or of the air velocity and/or of the relative humidity of the air and/or of the oxidizable air components occurs.

20. Arrangement according to claim 17, wherein the control device (6) and the ionization apparatus (2) are connected such that upon occurrence of a value of ozone that is too high the ozone value is reduced by decomposition, wherein the ionization apparatus (2) is controlled by a temporally supplied periodic alternating voltage as at least one alternating pulse, alternating pulse rate, or at least one packet with a predetermined sequence of alternating pulses.

21. Arrangement according to claim 18, wherein the control device (6) and the ionization apparatus (2) are connected such that for a contents of ozone in the supply conduit (8) of greater/identical to 0.06 ppm the power of the ionization apparatus (2) is lowered and wherein upon further increase of the value of ozone the time is changed of the supplied periodic alternating voltage as alternating pulse, alternating pulse rate, and/or packet of alternating pulses of a certain number.

* * * * *